United States Patent [19]

Toshima et al.

[11] Patent Number: 5,288,645
[45] Date of Patent: Feb. 22, 1994

[54] HYDROGEN EVOLUTION ANALYZER

[75] Inventors: Masato Toshima, Sunnyvale; Jerry Wong, Fremont, both of Calif.

[73] Assignee: MTM Engineering, Inc., Santa Clara, Calif.

[21] Appl. No.: 940,687

[22] Filed: Sep. 4, 1992

[51] Int. Cl.$^5$ ............................................. G01N 33/00
[52] U.S. Cl. .................................... 436/144; 436/127; 73/19.01; 73/19.07; 422/80
[58] Field of Search ................... 422/80; 436/144, 127; 73/19

[56] References Cited

U.S. PATENT DOCUMENTS

| | | | |
|---|---|---|---|
| 2,932,558 | 4/1960 | Bennet | 436/144 |
| 3,062,624 | 11/1962 | Peifer | 436/75 |
| 3,148,032 | 9/1964 | Bennet et al. | 422/80 |
| 4,098,576 | 7/1978 | Judge | 436/75 |
| 4,229,412 | 10/1980 | Orths et al. | 422/80 |
| 4,305,906 | 12/1981 | Mikasa et al. | 422/62 |
| 4,698,314 | 10/1987 | Tao | 436/171 |
| 4,784,833 | 11/1988 | Martin et al. | 422/80 |
| 4,800,747 | 1/1989 | Tsuji et al. | 73/19 |

OTHER PUBLICATIONS

W., A. Landford, M. J. Rand, 1978, "The Hydrogen content of Plasma-Deposited Silicon Nitride", Journal of Applied Physics, pp. 2473-2477.
W. Beyer, J. Herion, H. Wagner U. Zastrow, "Hydrogen Stability in Hydrogenated Amorphous Silicon Based Alloys", 1991, Materials Research Society Symposium vol. 219, pp. 81-86.
J. Neal, G. Shergill, M. Rose, J. K. Chu, "Quantitative Measurement of the Moisture Content in Thin Films", Jun. 1990, VMIC Conference, pp. 419-424.

*Primary Examiner*—James C. Housel
*Assistant Examiner*—N. Bhat
*Attorney, Agent, or Firm*—Hickman & Beyer

[57] ABSTRACT

Method for determining temperature ranges at which a selected gas evolves from a specimen of a selected material, bulk or surface of a metal, semiconductor, or insulator, and the probable source of that gas in each such temperature range. A specimen is placed in an evacuated and baked-out tube, and the specimen temperature T is increased according to a selected time-dependent temperature pattern over a temperature range. As temperature $T(t)$ increases, pressure $p(t)$ of any gas evolving in the tube is measured for a sequence of times t. A total pressure derivative, $dp/dT=(dp/dt)(dT/dt)^{-1}$, is determined, identifying one or more peak temperatures, each having a peak temperature range corresponding to specimen emission of at least one gas by breaking a bond containing an atom or molecule of that emitted gas. Partial pressure rises in the tube at each peak temperature are monitored and converted to an equivalent gas concentration. In a second embodiment, two tubes, with only one containing a specimen, are used for analyzing the differential pressure $\Delta p=p1-p2$ and differential pressure derivative $d(\Delta p)/dT$. In a third embodiment, both tubes contain specimens, and one or more peak temperatures are identified. In each embodiment, composition, partial pressures and concentrations of gases evolved at a peak temperature are optionally determined by residual gas analysis of another specimen in another tube, heated to and held at a peak temperature.

15 Claims, 8 Drawing Sheets

HYDROGEN EVOLUTION ANALYZER

BACKGROUND OF THE INVENTION

1. Field of the Invention

This invention relates generally to analytical instruments and more particularly to instruments that detect trace amounts of gases.

2. Background of the Technical Art

Plasma deposition of silicon nitride, silicon dioxide or amorphous silicon is a common processing step in fabrication of integrated circuits (ICs) in active matrix liquid crystal displays. Plasma deposition of such material usually occurs at low pressures, promoted by the presence of energy from a radiofrequency discharge or similar energy source.

Plasma deposition differs from deposition of pyrolytic silicon nitride and similar insulator materials by chemical vapor deposition (CVD) techniques in several respects. First, considerable bond scrambling occurs, wherein some bonds are broken and other bonds, which give rise to different molecular species, are formed. Second, plasma-deposited silicon nitride has no fixed stoichiometry (such as $Si_3N_4$) and is more accurately described as a polysilazane, $Si_xN_yH_z$, containing varying combinations of Si, N and H.

Semiconductor device performance often degrades after silicon nitride is used as a final passivation film for an IC, or after an anneal cycle to reduce plasma damage or improve electrical contact resistance. Silicon nitride has low hydrogen permeability so that free hydrogen can become trapped under a silicon nitride layer, or within this layer. Hydrogen evolution during subsequent high temperature processing is often the cause of such degradation, but IC manufacturers have had only limited methods to determine how such evolution occurs. The presence of hydrogen in plasma-deposited silicon nitride is confirmed by absorption spectrum analysis of such a compound, which manifests N—H and Si—H stretching bonds at the well known wavenumbers of 3350 $cm^{-1}$ and 2160 $cm^{-1}$, respectively.

The hydrogen evolved during subsequent application of high temperatures may be lightly bound interstitial hydrogen or may arise from bond breaking in compounds such as SiH and $SiH_2$ in hydrogenated amorphous silicon (a-Si:H), NH and $NH_2$ in nitride, and SiOH and trapped $H_2O$ in oxide films. The particular bonds that are present are important because different bonds are broken in different temperature ranges, and a temperature cycle for a particular process may include some or all of these temperature ranges.

Plasma-deposited silicon nitride, used as an encapsulant, as a gate dielectric and as an etch stop for IC fabrication, has been observed to degrade after cycling through the high temperatures used for annealing, for cure of plasma damage, for improvement of contact resistance, or for general semiconductor processing. The presence of hydrogen has been determined to be responsible, in large part, for this degradation. Plasma-deposited silicon nitride has no fixed stoichiometry and is best described by the general chemical formula $Si_xH_yN_z$, with x, y and z variable. Plasma-deposited silicon nitride often contains 10-30 atomic percent hydrogen, as interstitial hydrogen or in a chemical form such as $SiH_2$, $NH_2$, SiH or NH. The bonding strengths of the four molecules $SiH_2$, $NH_2$, SiH or NH differ and are known to increase in that order. Silicon nitride, once formed, has low permeability to hydrogen and $H_2O$ and can trap hydrogen evolved from the layer below the passivation film. It is difficult to determine the source(s) of the hydrogen that degrades the silicon nitride film, and no equipment is presently available that allows identification of the source(s) of this hydrogen.

A similar problem is encountered in use of amorphous silicon films for active matrix LCDs, solar cells and other photo-imaging tools. Amorphous silicon is often prepared using plasma-enhanced chemical vapor deposition, and the hydrogen content in a-Si:H is typically 10 atomic percent. The stoichiometry of a-Si:H is also not fixed, and this compound is best described by the chemical formula $SiH_y$ with y variable. Free hydrogen in a-Si:H passivates the dangling bonds and reduces the spin density so that the field effect charge carrier mobility in a thin film transistor increases. The carrier mobility value determines whether the a-Si:H film is suitable for AMCLD applications. Thus, it is important to determine the hydrogen content and hydrogen source(s) for amorphous silicon films.

Silicon nitride is used as a gate dielectric etch stopper and for passivation in AMCLD. Device reliability heavily depends upon the hydrogen bond stability in the silicon nitride film.

Lanford and Rand, in Jour. Appl. Phys., vol. 49 (1978) pp. 2473-2477, have determined the hydrogen content of plasma-deposited silicon nitride, using a nuclear reaction $H+N^{15}\rightarrow C^{12}+He^4+\gamma$-ray (4.43 MeV) in which the number of 4.43 MeV $\gamma$-rays emitted is proportional to the concentration of H present. Over a ratio range Si/N=0.7-1.4, the hydrogen content varied between $1.6\times10^{21}$ and $2.1\times10^{21}$ ($cm^{-3}$). This method of determining the amount of hydrogen present is expensive and does not, by itself, indicate the chemical forms in which the hydrogen is bound in the plasma-deposited material. As a result, this technique will not determine whether or not the hydrogen present will cause problems.

Beyer et al, in Jour. Appl. Phys., vol. 53 (1982) pp. 8745-8754, and in Materials Research Society Symposium, vol. 219 (1991) pp. 81-86, discuss hydrogen stability in hydrogenated amorphous semiconductor compounds, such as a-Si:H, a-Ge:H, a-Si—Ge:H, a-Si—N:H and a-Ge—N:H. The authors heat the individual hydrogenated compounds in a vacuum and use a quadrupole mass analyzer to identify hydrogen evolution and evolution rate at temperatures T=200°-800° C. Time rate of change of gas pressure is determined for particular species. One or more peaks of hydrogen evolution rate occur for amorphous silicon and nitride alloys. The technique is applied to study of diffusion characteristics of hydrogen for a-Si:H and silicon nitride but is not applied to study total hydrogen concentration and bonding.

Another technique sometimes applied, Fourier transfer infrared spectroscopy (FTIR), provides measurements on bonded hydrogen only. The Si—H and N—H absorption bands are well isolated, but calibration is critical and must usually be redone each time the spectroscopic instrument is used. The FTIR approach gives no information about the presence of interstitial hydrogen. The quantitative results are not always clear here, and FTIR provides no direct information on hydrogen evolution.

Sakka et al, in Appl. Phys. Lett., vol. 55 (1989) pp. 1068-1070, discuss hydrogen evolution from plasma-deposited, hydrogenated amorphous silicon films prepared from an SiH$_4$/H$_2$ mixture, using apparatus similar to that of Beyer et al, supra. Sakka et al indicate that hydrogen evolution is determined in part by the deposition conditions for the SiH$_4$ fraction rather than by diffusion characteristics. The Sakka et al technique is not used to determine hydrogen concentration.

It is desirable to determine the total amount of hydrogen present in a material that will be processed over a temperature range including high temperatures. It is also desirable to determine the hydrogen bonding strength and the chemical forms in which the hydrogen is bound on the IC. It is further desirable to estimate the temperature range or ranges at which large amounts of this hydrogen will be released during subsequent processing of the IC.

SUMMARY OF THE INVENTION

These needs are met by the invention, which provides method and apparatus for determining the relative and/or absolute amounts of hydrogen present in a material such as silicon nitride by analysis of a temperature profile of hydrogen evolution in such a material. In one embodiment of the method, one or more specimens (wafer test pieces) are inserted in a quartz or similar tube or other chamber, and the tube is sealed. The tube pressure is then reduced to a selected pressure of the order of one millitorr (0.133 Pa) to one Torr. The tube temperature is then raised, either to a selected temperature $T_1$, or at a selected rate $\Delta T / \Delta t \approx$ several degrees C/min to a selected temperature T(upper), and spectroscopic measurements of the pressure of hydrogen or other gas emitted p(t) by the specimen within the tube are taken as a function of time t. The pressure derivative with respect to temperature, $dp/dT = (dp/dt)(dT/dt)^{-1}$, of the hydrogen gas emission rate is also determined.

The pressure derivative dp/dT will manifest a sequence of isolated peaks in various temperature ranges. For example, the temperature ranges T = 350°-400° C., 450°-750° C. and 800°-1150° C., correspond to evolution of hydrogen gas from breaking of bonds such as Si—H$_2$, Si—H and N—H bonds, respectively. At a lower temperature range T = 100°-300° C., another peak of dp/dT will occur, corresponding to emission of hydrogen gas (H$_2$) that is lightly bound in interstitial positions within the material, or emission of H$_2$O that is absorbed by the oxide film. The tube is held at an upper temperature T(upper) for a selected time interval $\Delta t$. Total gas pressure is measured at each peak of the pressure derivative dp/dT and converted to equivalent hydrogen concentration. The tube temperature is then reduced to room temperature, the tube's gaseous contents are vented to the atmosphere, and the tube is opened to remove the specimen, if desired.

In a second embodiment of the method, two quartz tubes or other chambers are used, with one or more test specimens being placed in only the first tube. The second tube is empty or contains an uncoated substrate (collectively referred to as a control sample herein). The two tubes are subjected to the same pressurization and temperature treatments. Measured gas evolution in the second tube is subtracted from measured gas evolution in the first tube containing the specimen(s) to form a difference gas pressure $\Delta p = p_1 - p_2$, to characterize any moisture, residual gases and interstitial hydrogen that are emitted from the specimen at all temperatures and to compensate for background emissions from a tube or an uncoated sample. The temperatures T1(t) and T2(t) of the first and second tubes, respectively, are increased at a selected rate ($\approx 10°$ C./min), and the temperature is swept over the entire range of interest to map out the general shape of the curve and to determine the temperature ranges containing individual peaks of the evolution pressure derivative $d(\Delta p)/dT$. Total gas pressure is measured at each peak of the pressure derivative $d(\Delta p)/dT$ and converted to equivalent hydrogen concentration. Optionally, the measurements can be done separately in the two tubes to determine the moisture, residual gases and interstitial hydrogen emitted by the two tube interiors.

In a third embodiment, two tubes are prepared as in the second embodiment, with one or more test specimens being placed only in the first tube. Pressurization of the first tube interior proceeds as in the first embodiment. The temperature T = T1(t) of the first tube is increased at a relatively high rate ($\approx 10°$ C./min), and the tube temperature is swept over the entire range of interest, to map out the general shape of the pressure curve p1 and to determine one or more peak temperatures $T_p$ at which the evolution gas pressure derivative dp1/dT achieves a local maxima. The second tube temperature is then increased to a peak temperature $T_p$. Total gas pressure p2 is measured at one or more peak temperatures and is converted to equivalent concentrations of a target gas (e.g., hydrogen) at these temperatures. This third embodiment provides total hydrogen concentration in the important temperature regions where gas evolution rate is high. Gases other than hydrogen may be evolved and identified, and the temperature range at which each such gas is evolved may be important in subsequent IC processing steps carried out at relatively high temperatures (T $\geq$ 350° C.). In each embodiment, an additional tube containing a specimen may be provided to determine the composition of evolved gas at a peak temperature, by residual gas analysis.

DESCRIPTION OF THE PREFERRED EMBODIMENTS

Figure 1:
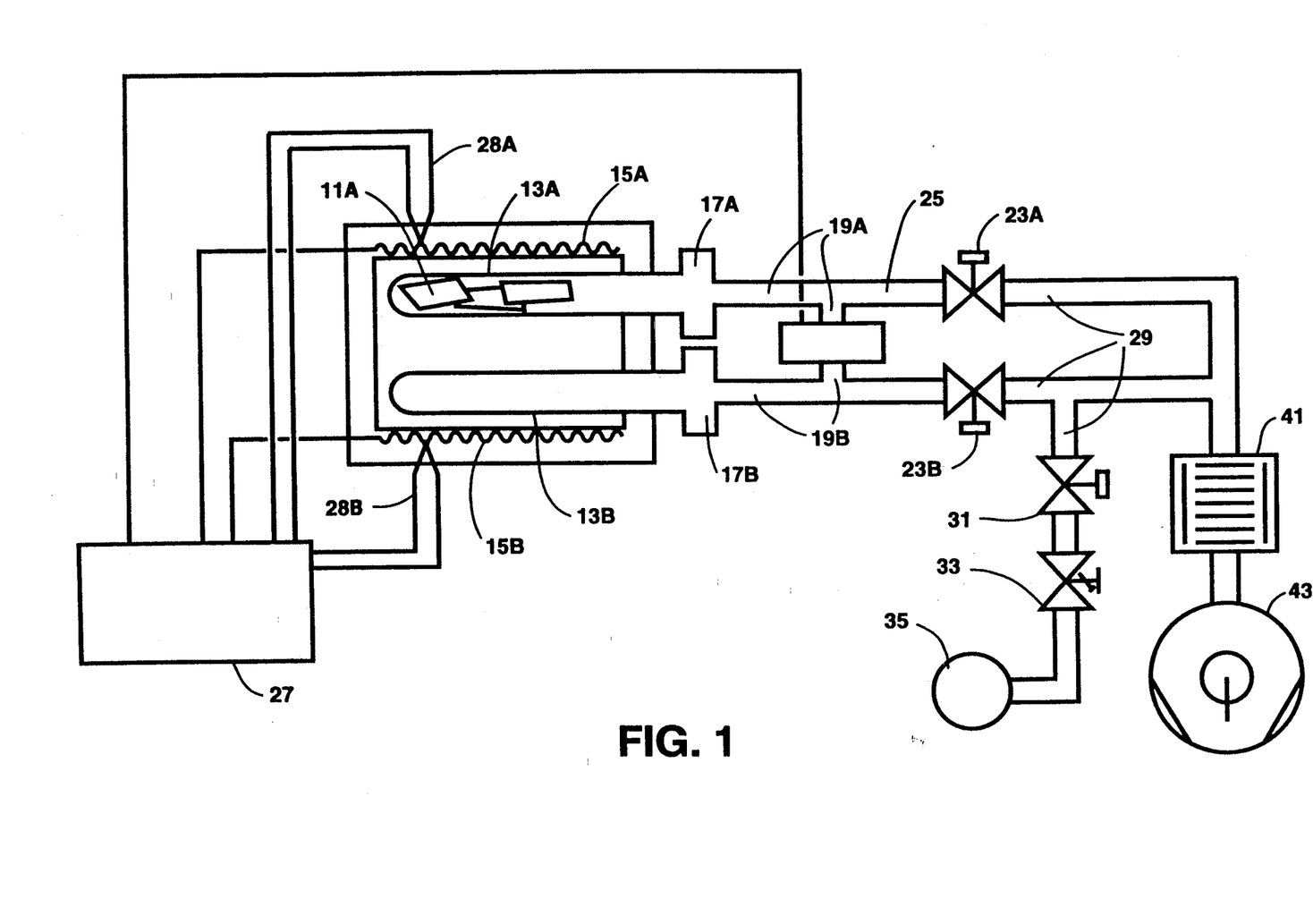
FIG. 1 illustrates an embodiment of the apparatus used to practice the invention, with two specimen tubes or, alternatively, with one specimen tube.

FIG. 1 illustrates a double-tube embodiment of the apparatus according to the invention. One or more integrated circuit specimens 11A are placed in a first tube 13A (and, optionally, in a second tube 13B), preferably made of quartz, and tube heaters 15A and 15B are positioned adjacent to or in contact with the specimen tubes. One end of each tube 13A and 13B is closed with a closure 17A and 17B, respectively, preferably including an O-ring, that can be opened to remove and replace specimens in each of the tubes. The tube closures 17A and 17B and specimen tube interiors communicate with first and second gas tubes 19A and 19B, respectively, that are connected to main shut-off valves 23A and 23B. A pressure gauge 25 is connected between the two gas tubes 19A and 19B to measure the gas pressures p1 and p2 and the pressure difference Δp=p1−p2 produced in these two tubes. The pressure gauge 25 is also connected to a data acquisition system 27.

The pressure gauge determines overall pressure of gas received from the interiors of the specimen tubes 13A and 13B. Where the presence of evolved hydrogen is to be sensed, the data acquisition system 27 may include a system that performs residual gas analysis of the gas constituents. The pressure gauge 25 determines overall pressure of gas received from the specimen tubes 13A and 13B. One or more thermocouples 28A and 28B are positioned contiguous to the respective tubes 13A and 13B to monitor and help control the temperature of that tube. The tube heaters 15A and 15B and thermocouples 28A and 28B are electrically connected to the data acquisition system 27, which controls the rate at which thermal energy is delivered to the specimen tubes 13A and 13B.

The shut-off valves 23A and 23B are connected by a manifold 29 to a purge gas valve 31, to an associated gas metering valve 33, and to a purge gas source 35 in series. The purge gas valve 31 and purge gas metering valve 33 deliver purge gas from the source 35 to the main shut-off valves 23A and 23B, for entry into and purging of the interiors of the specimen tubes 13A and 13B. The purge gas may be He, Ne, Ar, $H_2$, CO or some other relatively inert gas that has low concentration in the tube interiors.

The shut-off valves 23A and 23B are also connected by the third gas tube 29 through an oil mist trap 41 (optional) to a vacuum pump 43 that pumps down the interior of the specimen tubes 13A and 13B to a desired pressure, usually between 1 millitorr (0.133 Pa) and 1 Torr. The oil mist trap 41 also removes certain molecular debris from the gas within the system.

One or more specimens can be placed in each of the two specimen tubes 13A and 13B, or one of these tubes may be left empty. In a single tube embodiment of the apparatus shown in FIG. 1, the specimen tube 13B, the heater 15B, the tube seal 17B, the gas tube 19B and the shut-off valve 23B are omitted from the system.

Figure 2:
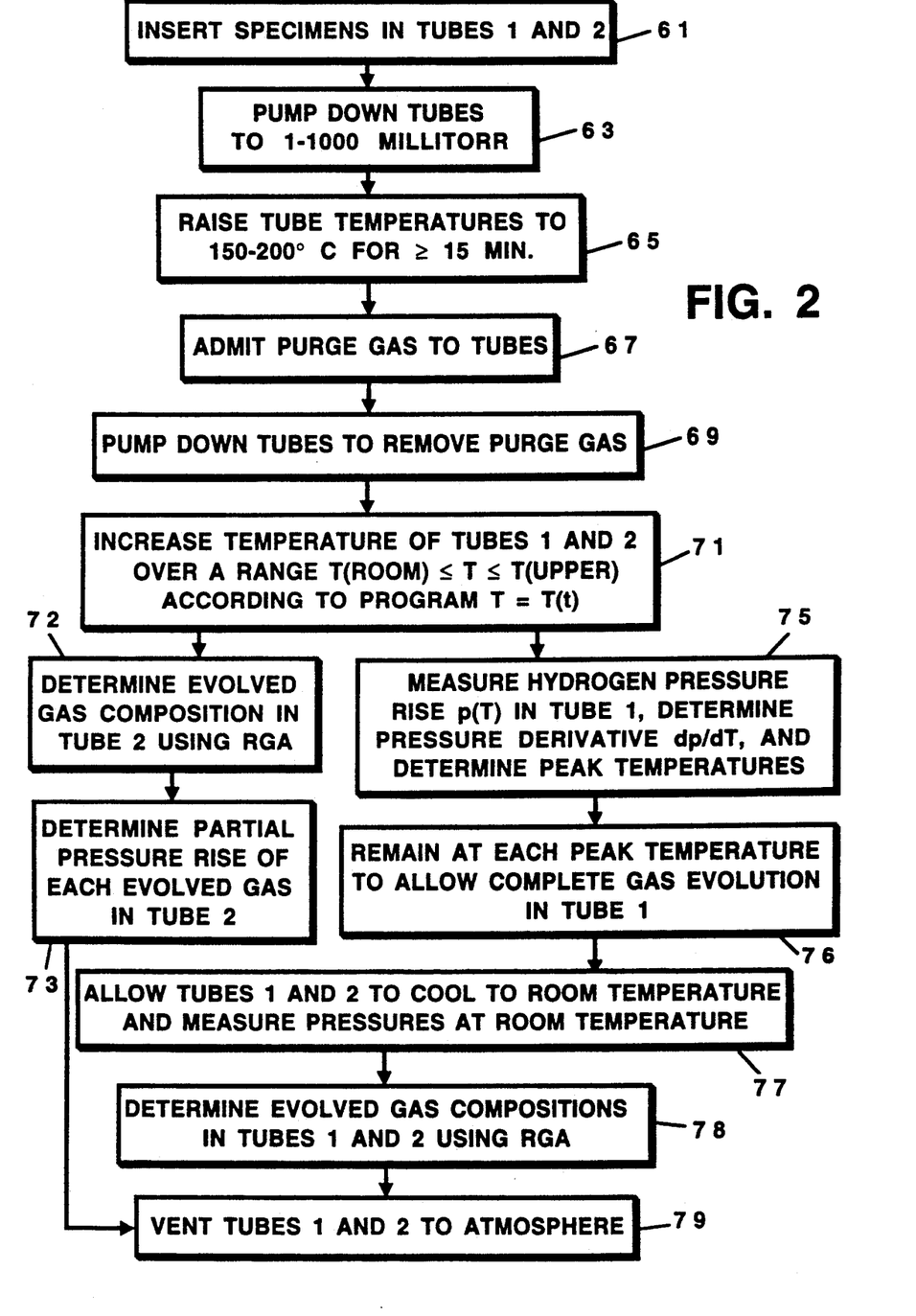
FIG. 2 is a flow chart of method steps used to practice the invention, using a single specimen tube for evolved gas pressure determination.

FIG. 2 is a flow chart illustrating a sequence of steps in a single-tube embodiment of the invention. One or more specimens are inserted into a specimen tube, such as 13A in FIG. 1, in step 61. In steps 63 and 65, the tube interior is pumped down to a pressure in the range 0.001–1 millitorr, and the temperature of the tube is raised to $T \leq 200°$ C. for a time interval $\Delta t \geq 15$ minutes, to bake out most or all of the impurities in the tube interior. In step 67, the shut-off valve (19A in FIG. 1), the purge gas shut-off valve (31 in FIG. 1) and the gas purge metering valve (33 in FIG. 1) are opened and the tube interior is filled with purge gas. The purge gas shut-off valve is then closed, and the purge gas is removed from the tube interior, by pumping down or otherwise, in step 69. Steps 67 and 69 may optionally be repeated one or more times to more thoroughly purge the tube interior. A second tube containing a similar specimen, for analysis of the composition of the evolved gas, is optionally subjected to the steps 61–69.

In step 71, the shut-off valve (23A in FIG. 1), is then closed, and the temperature T(t) of the first tube and the optional second tube is increased through a continuous range or discrete sequence of steps, from room temperature to a selected upper bound T=T(upper) (as high as 1150° C.) as a function of time t. This produces a programmed similar temperature rise in the specimen(s) in the tube interior(s). Pressure rise in the tube interior(s) is continuously monitored through a pressure gauge (25 in FIG. 1). As the specimen temperature S(t) rises, hydrogen bonds and other bonds are broken and hydrogen gas (and possibly other gases) evolves. The (narrow) temperature range in which hydrogen is driven off is characteristic for a particular bond energy and diffusion characteristic, in a manner resembling destructive distillation or "cracking" of petroleum to produce different petroleum products. For example, hydrogen bonds are broken and hydrogen gas is given off a silicon surface at certain characteristic temperature ranges. As this hydrogen gas evolves, the pressure p in the chamber rises.

Figure 3:
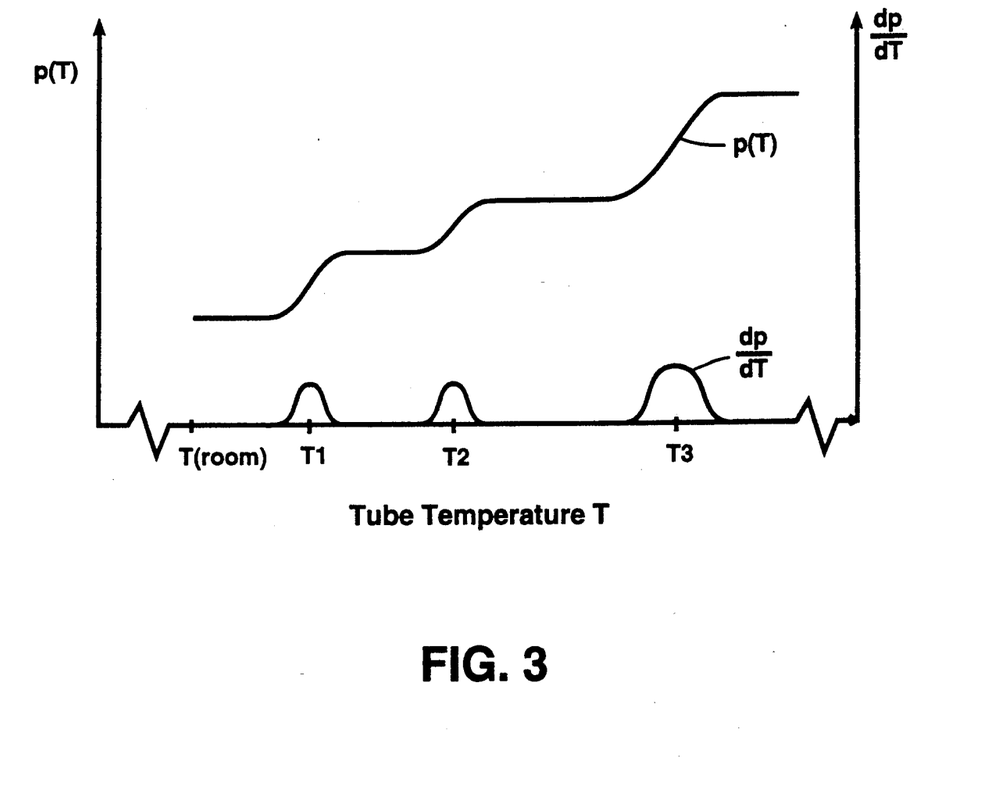
FIG. 3 is a plot of evolved gas pressure and thermal derivative of this pressure for a representative specimen.

FIG. 3 qualitatively illustrates the traces of pressure p(T) and a derivative dp/dT that might be obtained for a representative specimen subjected to a programmed temperature rise by the apparatus shown in FIG. 1. Because the tube temperature T(t) is programmed, this temperature is known with reasonable accuracy at all times t. The curve dp/dT includes a sequence of bell-shaped curves centered at the peak temperatures $T=T_{1p}, T_{2p}, T_{3p}$, etc. Each peak temperature has an surrounding temperature range where dp/dT is greater than a selected small positive number δ. Preferably, these temperature ranges for the curve dp/dT should not overlap. The peak temperatures $T_{1p}, T_{2p}, T_{3p}$, etc. may correspond to mid-points of the temperature ranges set forth in Table 1.

Table 1 sets forth suitable temperature ranges for gas evolution in a silicon-containing specimen. However, the methods and apparati disclosed here are applicable to evolution of other gases from the surface or bulk of a metal (such as W or Ti), a semiconductor (such as Si), or an insulator (such as $SiO_x$ or $Si_xN_y$).

TABLE 1

| Temperature Ranges For Evolution of Hydrogen. | | | |
|---|---|---|---|
| Unbroken Bond | Bond Broken | $H_2$ Evolution Temperatures | $H_2O$ Evolution Temperatures |
| Interstatial $H_2$ | | $T \leq 300°$ C. | $T \leq 200°$ C. |
| Surface $H_2O$ | | | $150°$ C. $\leq T \leq 400°$ C. |
| Bulk $H_2O$ | | | $450°$ C. $\leq T \leq 650°$ C. |
| | SiOH | $550 \leq T \leq 900°$ C. | |
| | $SiH_2$ | $350 \leq T \leq 400°$ C. | |
| | SiH | $450 \leq T \leq 750°$ C. | |
| | NH | $800 \leq T \leq 1150°$ C. | |

One uncertainty here is the source of an experimentally observed pressure rise in the temperature range $450°$ C. $\leq T \leq 650°$ C. This pressure rise can arise from either breaking of an SiOH bond or from release of more tightly bound $H_2O$, or both, and Table 1 reflects this uncertainty. Cox, Shergill, Rose and Chu from Intel, in "Quantitative Measurement of the Moisture Content in Thin Films", VMIC Conference, Jun. 12–13, 1990, pp. 419–424, describe evolution from thin oxide films in the temperature range $450°$ C. $\leq T \leq 650°$ C. of a gas that is believed to be $H_2O$. Other workers have suggested that breaking of a bond in SiOH produces a pressure rise in this range. At this time, the source or sources of a pressure rise in the range $450°$ C. $\leq T \leq 650°$ C. is not specifiable.

In step 72 of FIG. 2, the evolved gas composition in the second tube is analyzed spectroscopically or otherwise to determine the evolved gas composition and to determine the equivalent concentration of the target specie, for example hydrogen. Residual gas analysis (RGA) is preferably used for this purpose. One appropriate RGA instrument is available from MKS Instruments, Santa Clara, Calif. Used with quadrupole mass analysis, this apparatus is suitable for determining the presence and fraction of many gases, including $H_2$, OH and $H_2O$. The partial pressure p2, if significant, of each gas evolved in the second tube is determined in step 73. Steps 72 and 73 are optional and are helpful in more precisely determining the concentration of the target specie evolved at a given temperature.

In step 75, the total pressure $p1(T(t))$ of the evolved gas(es) in tube 1 is measured and the pressure derivative with respect to temperature, $dp1/dT = (dp1/dt)(dT/dt)^{-1}$, is determined simultaneously for the gas specie(s) evolved. "Peak" temperatures $T = T_{1p}, T_{2p}, T_{3p}$, etc., where the curve $dp1/dT$ attains a local maximum as temperature changes, are identified. Each peak temperature corresponds to a high evolution rate of $H_2$ (or other gas of interest) from broken bonds in the specimen in tube 1.

In step 76 of FIG. 2, the temperatures of the first tube and second tube remain at or near a peak temperature for a time sufficient to allow evolution of almost all gas that can be released at that peak temperature.

In step 77, the first tube is allowed to cool to room temperature T(room), and pressure in the first tube interior is again measured (optional). In step 78, the composition of the evolved gases at room temperature in the first tube is determined, using residual gas analysis. In step 79, the pressure gauge is isolated, and gases in the two tubes are vented to the atmosphere.

Figure 4:
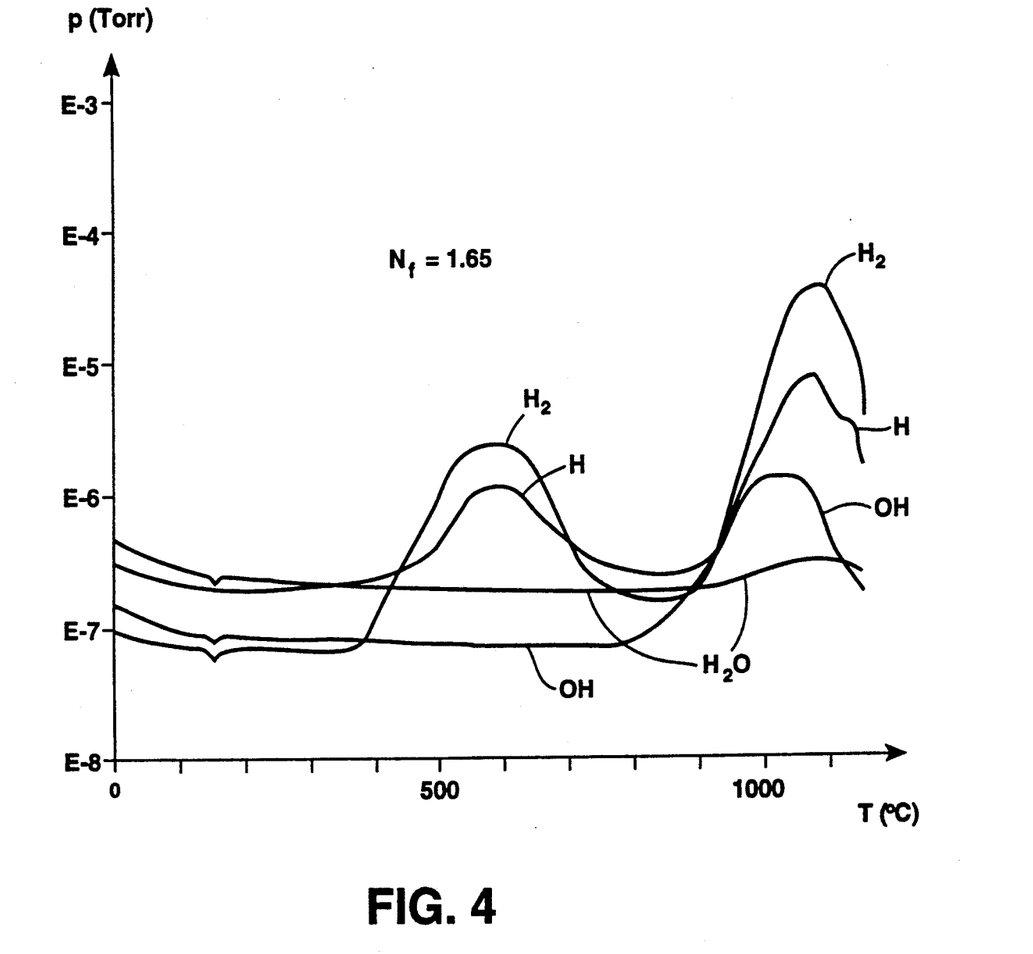
FIG. 4 is a plot illustrating residual gas analysis that helps determine evolved gas composition.

FIG. 4 is a plot of the partial pressures of gases evolved from a wafer of hydrogenated silicon oxynitride, where the atomic weight ratio of nitrogen to oxygen present is $N_f = 1.65$. Note that the partial pressures of H and $H_2$ have broad peaks centered near the same pair of temperatures, $T \approx 600°$ C. and $T \approx 1050°$ C., with these partial pressures at $T \approx 1050°$ C. being about one order of magnitude higher than these partial pressures at $T \approx 600°$ C. The partial pressure of OH peaks near $T \approx 1000°$ C., and the $H_2O$ has a broad peak near $T \approx 1050°$ C. after decreasing to a minimum at lower temperatures. The higher and lower temperature peaks for $H_2$ (or H) may arise from hydrogen evolution from NH and from SiH, respectively. The OH may arise from breakup of SiOH molecules. The $H_2O$ may arise from liberation of bound water from the surface and/or bulk of the wafer material. If the nitrogen ratio $N_f$ is increased above 1.65, to 1.80 for example, the magnitude of the lower temperature partial pressure peak for $H_2$ will rise relative to the magnitude of the higher temperature partial pressure peak for $H_2$.

Figure 5A:
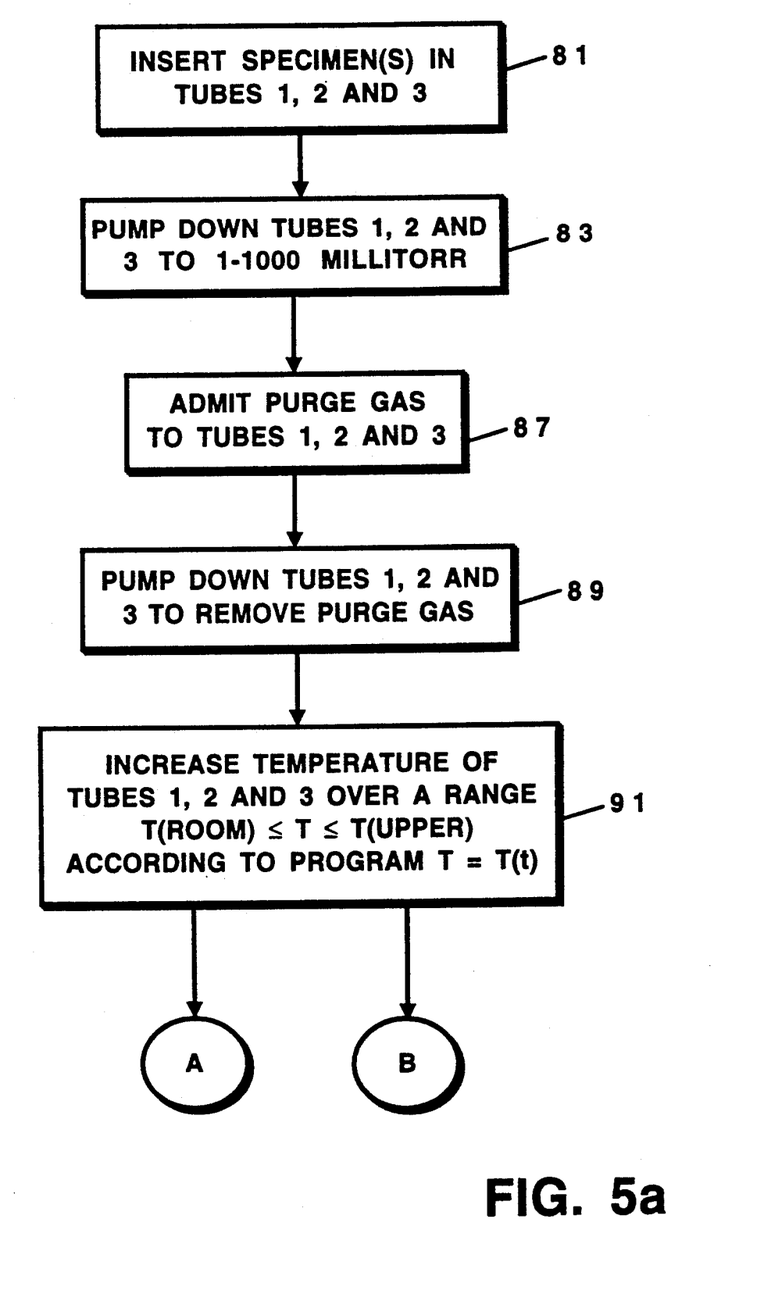
FIGS. 5a and 5b and 6a and 6b are flow charts of method steps used to practice the invention using two specimen tubes, according to two other embodiments of the invention.
Figure 5B:
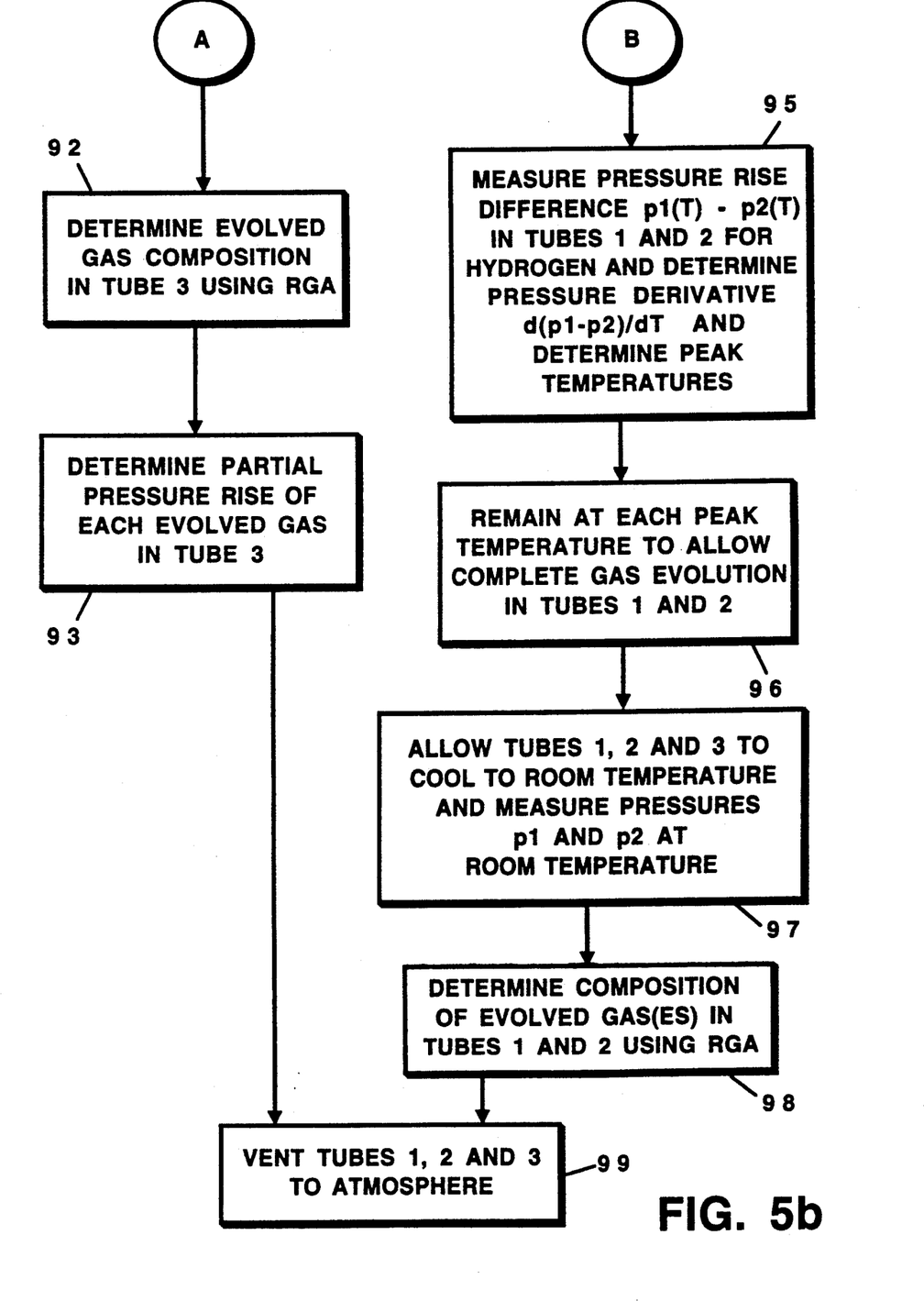

FIG. 5 (5A/5B) is a flow chart illustrating a sequence of steps in a double-tube embodiment of the invention, in which a first tube contains one or more specimens and a second tube contains either no specimen, an uncoated substrate or a substrate coated with an oxide layer and/or a nitride layer and is used for background measurements. For ease of reference, the contents of the second tube, empty or containing an uncoated substrate, will be referred to as a "control sample" herein. Optionally, a third tube containing a similar specimen is provided for analysis of evolved gas composition at one or more peak temperatures for the third tube specimen. Preferably, the two (or three) tubes should be as identical as possible, before a specimen is placed in a tube. One or more specimens is inserted into specimen tubes 1 and 3, in step 81. Tube 2 contains a control sample and is used as a background tube. In step 83, the tube interiors are pumped down to a pressure in the range 0.001–1 Torr. Step 83 is optional, because tube 2 is being used as a control sample tube here. In step 87, the purge gas shut-off valve and the gas purge metering valve are opened, the tube interiors are filled with purge gas, and the purge gas shut-off valve is closed. The purge gas is then removed from the tube interiors, by pumping down or otherwise, in step 89. Steps 87 and 89 may optionally be repeated one or more times to more thoroughly purge the tube interiors.

In step 91, the shut-off valves (23A and 23B in FIG. 1) are then closed, and the three tube temperatures T1(t), T2(t) and T3(t) are increased through a continuous range or discrete sequence of steps, from room temperature to a selected upper bound T = T(upper) (as high as 1150° C.) as a function of time t. Pressure rise in each tube is continuously measured through a pressure gauge (25 in FIG. 1). This produces a programmed similar temperature rise in the specimen(s) in the tube 1 and tube 3 interiors. As the specimen temperatures rise, hydrogen gas $H_2$ that is contained on or in the specimen material will be driven off, as discussed above.

In steps 92 and 93, the composition and partial pressures of the evolved gas(es) in tube 3 are analyzed, using a residual gas analyzer or other suitable gas analysis means, and this pressure is converted to an equivalent gas concentration for the target gas. This measurement confirms (or refutes) the hypothesis that this gas is mainly hydrogen or another target gas, with other gases usually having negligible concentrations, and provides a reasonably accurate concentration value.

In step 95, the total pressure rises p1(T) and p2(T) and the pressure difference $\Delta p = p1 - p2$ in the first and second tubes are determined for one or more gas constituents, and the pressure derivative $d(\Delta p)/dT$ is determined for the gas(es) evolved. Simultaneously, as the tube temperature rises, peak temperatures $T = T_p$, corresponding to the various peaks of $d(\Delta p)/dT$, are identified. Each peak temperature itself serves as an indicia for the particular chemical bonds being broken near such peak temperature for the specimen. In step 96, the temperature will remain at $T = T_p$ until the total pressure time derivative dp/dt decreases to a selected minimum value, such as a reference gas leakage value, to allow complete gas evolution at that temperature.

FIG. 3 also illustrates the traces of pressure difference $\Delta p(T)$ and $d(\Delta p)/dT$ that might be obtained for a representative specimen in tube 1 and control sample in tube 2 subjected to a programmed temperature rise by the apparatus shown in FIG. 1. Here, the pressure arising from any background gases emitted by a "bare" tube or by an uncoated substrate in a tube are assumed to be compensated for by forming the pressure difference $\Delta p(T)$.

In step 97 of FIG. 5, the tubes 1 and 2 are allowed to cool to room temperature, and the partial pressures in each tube are measured. In step 98, the composition of the evolved gas(es) in the first and second tube interiors and total hydrogen concentration are determined, for calculation purposes, using residual gas analysis. In step 99, the pressure gauge is isolated, and gas in the specimen tubes 1, 2 and 3 is vented.

Figure 6A:
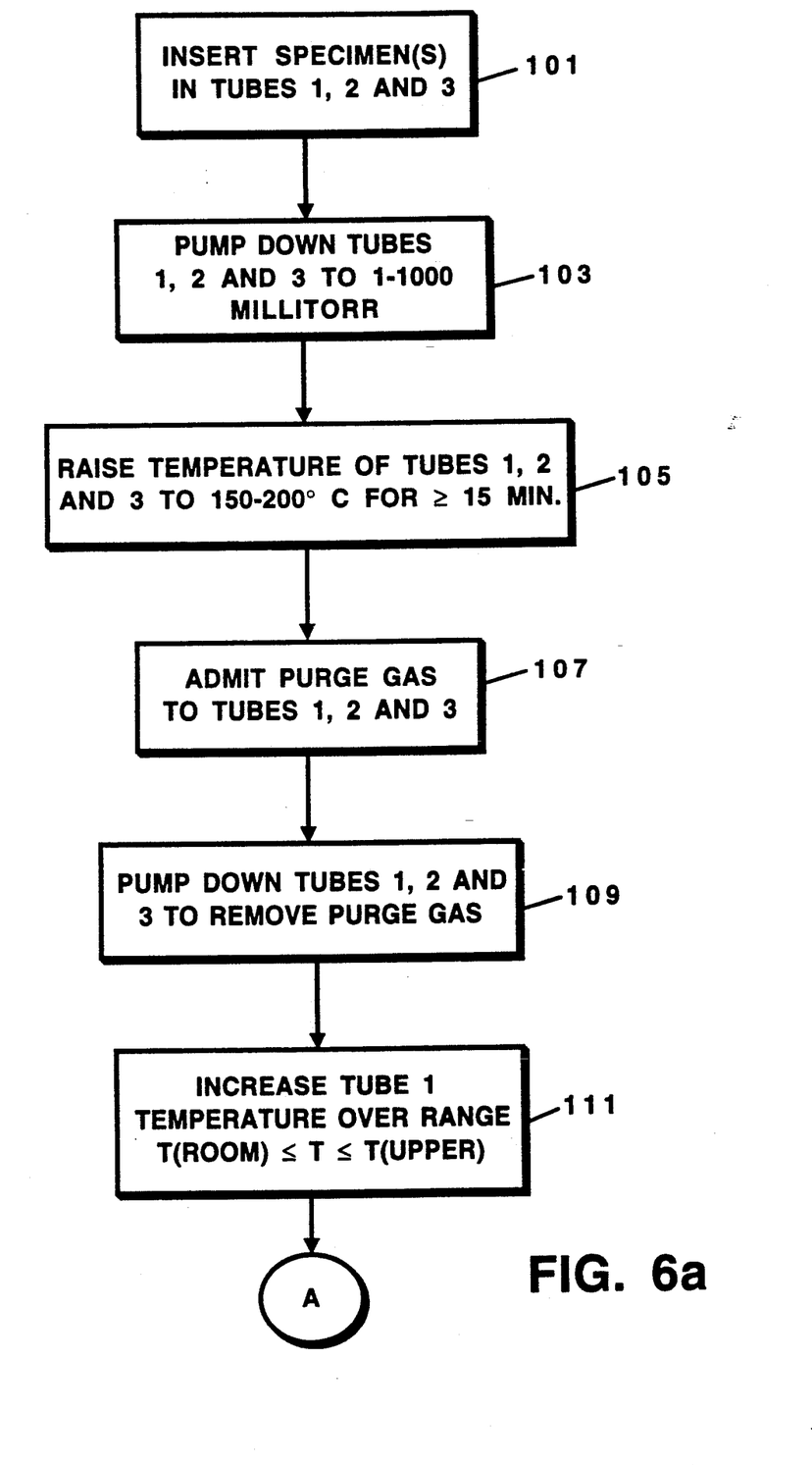
Figure 6B:
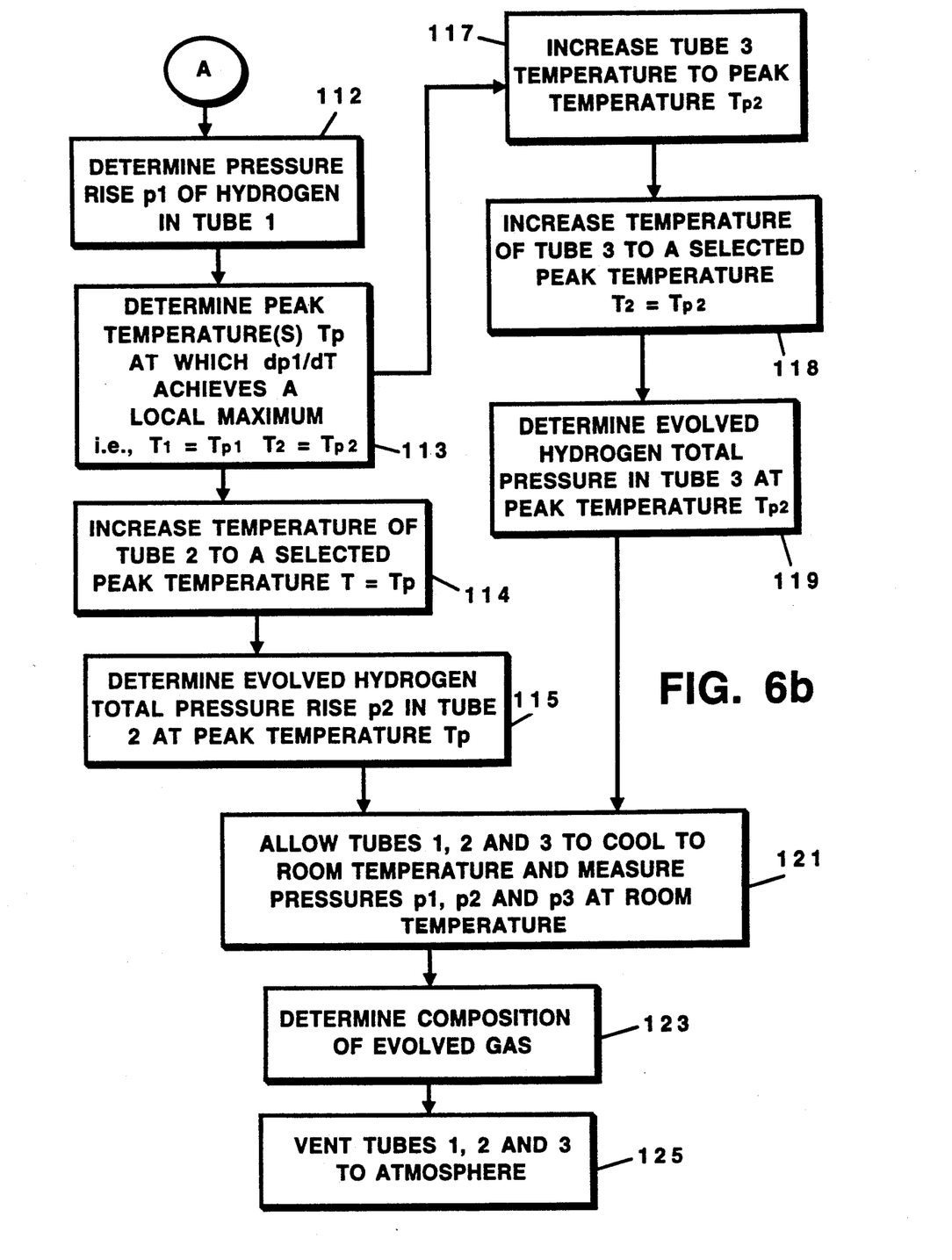

FIG. 6 (6A/6B) is a flow chart illustrating a sequence of steps in a third (double-tube) embodiment of the invention, in which a first tube and a second tube contain one or more specimens each. Preferably, the two tubes should be as identical as possible. One or more specimens is inserted into each of specimen tubes 1 and 2, in step 101. Optionally, a similar specimen is inserted in a third tube, for gas composition analysis purposes. In step 103, the tube interiors are pumped down to a pressure in the range 0.001–1 Torr to remove most or all of the impurities in the tube interiors. In step 105, the temperatures of the three tubes are raised to 150°–200° C. for a time interval of length 15 minutes or more for outgassing.

In step 107, the shut-off valve, the gas purge shut-off valve and the gas purge metering valve are opened and the three tube interiors are filled with purge gas. The purge gas shut-off valve is then closed and the purge gas is removed from the tube interiors, by pumping down or otherwise, in step 109. Steps 107 and 109 may optionally be repeated one or more times to more thoroughly purge the tube interiors.

In step 111, the first tube temperature T1(t) is increased from room temperature to a selected temperature T(upper). The temperature T(upper) may be approximately equal to one of the bond breaking temperatures. As the specimen temperature rises, hydrogen gas $H_2$ or another target gas that is contained on or in the specimen material will be driven off, as discussed above. The rise in total pressure p1 and the derivative $dp1/dT = (dp1/dt)(dT/dt)^{-1}$ in tube 1 are measured in steps 112 and 113. The gas pressure derivative dp1/dT will attain one or more local maxima, thereby identifying one or more peak temperatures $T_p$.

In steps 114 and 115, the second tube temperature is increased to and held at or near a peak temperature $T_p$, and the gas total pressure rise $p2(T^p)$ is obtained at such peak temperature. Tube 2 is held at such peak temperature for a selected time interval $t_2 \leq t \leq t_2 + \Delta t_2$. This time interval may extend until the normal measured or reference gas leakage rate $(dp/dt)_{ref}$ from that tube containing gas at the same pressure exceeds the measured time derivative dp2/dt for the evolved gas pressure p2 in that tube.

In step 117, the temperature of tube 3 (optional) is increased to, and held at, a peak temperature $T_p$. In step 118 the composition of evolved gas in tube 3 is determined, using residual gas analysis or other gas composition analysis means. In step 119, the partial pressures and concentrations, if significant, of hydrogen and any other evolved gas species of interest are determined.

Alternatively, a new specimen is placed in the first tube, the first tube interior is pumped down and purged with purge gas, tubes 1 and 2 are raised to first and second peak temperatures $T_{1p}$ and $T_{2p}$, and gas pressures, compositions and hydrogen concentrations in the two tubes are determined, using RGA for the third tube. This alternative approach allows an increase in test specimen throughput.

In step 121, the specimen tubes 1, 2 and 3 are allowed to cool to room temperature T(room), and pressure in the tube interiors is again measured. In step 123, the composition of the evolved gases in tubes 1, 2 and 3 are determined, using residual gas analysis. In step 125, the pressure gauge is isolated, and gases in the specimen tubes 1, 2 and 3 are vented. In each of the pressure measurements, the tube pressures p1, p2 and/or p3 are converted to equivalent concentration of the target gas (e.g., hydrogen).

The pressure gauge 25 in FIG. 1 may have a pressure range p(lower)$\leq$p$\leq$p(upper) in which the gauge operates most reliably. If the gas pressure p generated in the tube interior is less than p(lower), a relatively inert buffer gas, such as He, Ne, Ar, $H_2$ or CO, of selected pressure p(buffer) may be added to the tube interior so that the sum of the partial pressures p(evolved gas)+p(buffer) lies in the range of maximum reliability for the pressure gauge when gas is generated from the specimen in the tube interior.

If the shape of the total pressure derivative curve $dp/dT$ or $d(\Delta p)/dT$ at or near one of the peaks of the curve, such as $T = T_{1p}$ in FIG. 3, is known accurately, the specimen temperature T need not be swept through a range of temperatures. The specimen can be heated to the peak temperature $T_{1p}$ of interest, and the value of the pressure derivative, $dp/dT$ or $d(\Delta p)/dT$, can be determined at or adjacent to a local maximum of this curve. The number of bonds broken near a peak value temperature such as $T = T_{1p}$ can then be determined from a knowledge of the peak value and the shape of this curve.

We claim:

1. A method for determining the amount of a selected gas that evolves from a specimen of a selected material, the probable source of that gas and the concentration of a selected element in the evolved gas, the method comprising the steps of:

inserting a specimen into the interior of an evacuable chamber and evacuating the chamber to a selected evacuation pressure;

increasing the specimen temperature T to at least one selected temperature and monitoring the pressure of any gas that appears in the chamber interior at the selected temperature; and determining the amount of a gas evolved in the chamber at temperatures near the selected specimen temperature by analyzing changes in the monitored pressure as the chamber temperature is increased.

2. The method of claim 1, further comprising the steps of:

providing a second evacuable chamber and evacuating the second chamber to said selected evacuation pressure;

increasing the temperature of the second chamber to said selected temperature and monitoring the pressure p2 of any gas that appears in the second chamber interior at said selected temperature; and determining the amount of a gas evolved in the second chamber at temperatures near said selected temperature.

3. The method of claim 2, further comprising the step of determining a pressure difference indicative of the pressure differential between gases in said first and second chambers at said selected temperature.

4. The method of claim 2, further comprising the step of inserting an uncoated substrate into the interior of said second chamber before said second chamber is evacuated.

5. The method of claim 2, further comprising the step of inserting a second specimen into said second chamber before said second chamber is evacuated.

6. The method of claim 2, further comprising the steps of:

determining the composition of gas generated in at least one of said first chamber and said second chamber at said selected temperature; and determining the concentration of the selected gas in said chambers.

7. The method of claim 6, wherein said step of determining said composition of said gas at said selected temperature comprises the steps of:

inserting a specimen into the interior of a third evacuable chamber and evacuating the third chamber to the selected evacuation pressure;

increasing the temperature of the third chamber to the selected temperature and determining the composition of any gas that appears in the third chamber interior at that temperature by residual gas analysis.

8. The method of claim 1, wherein said selected gas is selected from the group consisting of water vapor and hydrogen.

9. The method of claim 1, further comprising the steps of:

increasing said said chamber temperature T over a selected temperature range $T(lower) \leq T \leq T(upper)$ according to a selected time-dependent temperature pattern $T(t)$;

monitoring the pressure p of any gas that appears in said chamber interior as the temperature T changes and determining the thermal derivative $dp/dT$ of this pressure; and identifying one or more temperatures in the temperature range at which $dp/dT$ is always greater than a selected small positive number, which indicates that the temperature range corresponds to the emission of at least one gas from the specimen.

10. The method of claim 9, wherein:

said specimen contains Si; and said temperature range is selected from the group of ranges consisting of a first range $T \leq 200°$ C. in which surface $H_2O$ is released, a second range $150° C. \leq T \leq 400°$ C. in which bulk $H_2O$ is released, a third range $T \leq 300°$ C. in which interstitial hydrogen is released, a fourth range $350° C. \leq T \leq 400°$ C. in which a hydrogen bond in $SiH_2$ is broken, a fifth range $450° C. \leq T \leq 750°$ C. in which a hydrogen bond in SiH is broken, a sixth range $450° C. \leq T \leq 650°$ C. in which a bond in SiOH is broken or $H_2O$ is released, and a seventh range $800° C. \leq T \leq 1150°$ C. in which a hydrogen bond in NH is broken.

11. A method for determining the amount of a selected gas that evolves from a specimen of a selected material, the probable source of that gas and the concentration of a selected element in the evolved gas, the method comprising the steps of:

inserting a first test specimen into the interior of a first evacuable chamber and evacuating the first chamber to a selected evacuation pressure;

inserting a second test specimen into the interior of a second evacuable chamber and evacuating the second chamber to the selected evacuation pressure;

heating the first chamber to remove residual gases from the first chamber and the first test specimen;

determining one or more peak evolution temperatures at which the thermal derivative of a gas pressure p1 evolved in the first chamber by heating the first chamber achieves a local maximum;

heating the second chamber to remove residual gases from the second chamber and the second test specimen, wherein during the second chamber heating step, the second chamber temperature is increased to at least one of said peak evolution temperatures and held at such temperature for a period of time;

monitoring the pressure of any gases evolved in the first and second chambers during a selected time interval; and determining the amount of a gas evolved from the specimen at temperatures near the peak temperature by distinguishing changes in the monitored pressure as the chamber temperature is increased.

12. The method of claim 11, further comprising the steps of:

determining the composition of gas generated in said first and second chambers at said peak temperature; and determining the concentration of said selected gas in said chambers.

13. The method of claim 12, wherein said step of determining said composition of said gas at said selected temperature comprises the steps of:

inserting a specimen into the interior of a third evacuable chamber and evacuating the third chamber to the selected evacuation pressure;

increasing the temperature of the third chamber to the selected temperature and determining the composition of any gas that appears in the third chamber interior at that temperature by residual gas analysis.

14. The method of claim 11, wherein said selected gas is selected from the group consisting of water vapor and hydrogen.

15. A method for determining the amount of a selected gas that evolves from specimen of a selected material, the probable source of that gas and the concentration of a selected element in the evolved gas, the method comprising the steps of:

inserting a first specimen into the interior of a first evacuable chamber and a second specimen into the interior of a second evacuable chamber and evacuating the first chamber and the second chamber to a selected evacuation pressure;

increasing the first chamber temperature and the second chamber temperature to at least one selected temperature and monitoring the pressure of any gas that appears in the first and second chamber interiors at the selected temperature; and determining the amount of a gas evolved in the first chamber interior near the selected temperature by determining a pressure difference indicative of a pressure differential between gases in the first and second chambers.

* * * * *